United States Patent [19]

Dorn et al.

[11] 4,277,467

[45] Jul. 7, 1981

[54] ENDOPARASITICIDAL PASTES FOR HORSES

[75] Inventors: Hubert Dorn, Wuppertal; Herbert Voege, Leverkusen, both of Fed. Rep. of Germany

[73] Assignee: Bayer Aktiengesellschaft, Leverkusen, Fed. Rep. of Germany

[21] Appl. No.: 74,043

[22] Filed: Sep. 10, 1979

[30] Foreign Application Priority Data

Sep. 26, 1978 [DE] Fed. Rep. of Germany ....... 2841882

[51] Int. Cl.$^3$ ............................................. A61K 31/66
[52] U.S. Cl. ..................................... 424/217; 424/326
[58] Field of Search ............................... 424/217, 326

[56] References Cited

U.S. PATENT DOCUMENTS

| 3,331,738 | 7/1967 | Collins et al. | 424/217 |
| 3,937,825 | 2/1976 | Alford | 424/217 |
| 3,993,682 | 11/1976 | Kolling et al. | 424/326 |

FOREIGN PATENT DOCUMENTS 925769  5/1963  United Kingdom ..................... 424/217

OTHER PUBLICATIONS

Bello et al., Chem. Abstracts, vol. 80, abst. 116207d (1974).
Cook, Chem. Abstracts, vol. 81, abst. 9777p (1974)
Drudge et al., Chem. Abstracts, vol. 84, abst. 115893v (1976).
Blodinger, Chem. Abstracts. vol. 84, abst. 159,836h (1976).
Anon (Food Drug. Adm.), Chem. Abstracts, vol. 83, abst. 120699v (1975).
Chem. Abstracts, vol. 84, abstract 73949k (1976). (Abut. of Ger. Offen. 2,423,679).

Primary Examiner—John D. Randolph
Attorney, Agent, or Firm—Sprung, Felfe, Horn, Lynch & Kramer

[57] ABSTRACT

The invention relates to endoparasiticidally effective pastes containing mixtures of 2,2,2-trichloro-1-hydroxyethyl-phosphoric acid dimethyl ester and N-(2-methoxyacetamido-4-phenylthiophenyl)-N',N"-bis-methoxy-carbonylguanidine and includes a process for the production of said pastes as well as the use of said pastes.

8 Claims, No Drawings

ENDOPARASITICIDAL PASTES FOR HORSES

The present invention relates to new pastes, for horses, which have an endoparasiticidal action and contain, as the active constituents, a mixture of the two known individual active compounds 2,2,2-trichloro-1-hydroxyethylphosphonic acid dimethyl ester (=Trichlorfon) and N-(2-methoxyacetamido-4-phenylthiophenyl)-N',N''-bis-methoxycarbonylguanidine (=Febantel), to a process for their production and to their use.

Trichlorfon is known (see, for example, U.S. Pat. No. 2,701,255) and is active, in particular, against the following endoparasites of horses: Helminths, such as Ascaridae, Oxyurae and Habronema spp., but in addition also against Gasterophilus spp. (that is to say insect larvae which live preferably in the mouth and in the gastro-intestinal tract of horses).

Febantel is likewise known (see, for example, German Patent Specification No. 2,423,679 and U.S. Pat. No. 3,993,682) and is particularly outstandingly active against roundworms in the gastro-intestinal tract and lungs of horses and against the immature stages of these roundworms.

According to the present invention there is provided an endoparasiticidal paste, for horses, which comprises a mixture of Trichlorfon and Febantel and the water content of which is less than one percent by weight, relative to the total amount of the combination formulation.

Surprisingly, the endoparasiticidal pastes, according to the invention, for horses exhibit a synergistic (=superadditive) effect against endoparasites, and in particular against Strongylidae (species of roundworm) of horses.

Preferred pastes according to the present invention contain 5 to 70, in particular 20 to 60, parts by weight of Trichlorfon, 0.5 to 10, in particular 2 to 8, parts by weight of Febantel, 20 to 70, in particular 30 to 60, parts by weight of liquid and/or semi-solid carrier(s), 0 to 20, in particular 0 to 10, parts by weight of one or more additives and 0 to 1, in particular less than 0.5, part by weight of water.

Paraffin hydrocarbons, preferably mineral oils, for example liquid paraffin, are preferably employed as liquid and/or semi-solid carriers.

By the term "mineral oil" there are to be understood all liquid and/or semi-solid aliphatic hydrocarbons of mineral origin. Mineral oil is preferable to vegetable oils, since it does not become rancid and is not digested and the stability of the active compounds therein is better. The mineral oils employed (for example paraffin) are liquid or semi-solid (for example petroleum jelly) and preferably contain aliphatic hydrocarbon chains with 16 to 60 carbon atoms.

Possible additives are thickeners, stabilisers, wetting agents and/or emulsifiers and perfumes and/or flavour-improving substances.

Thickeners which may be mentioned are: inorganic thickeners, such as silicates, for example bentonites or colloidal silica, and organic thickeners, such as fatty alcohols or fatty acid esters (such as, for example, hydrogenated castor oil).

Stabilisers which may be mentioned are antioxidants (for example butylhydroxyanisole).

An example of a possible wetting agent is: sodium lauryl-sulphate.

Examples of possible emulsifiers are alcohols, such as: cetyl-stearyl alcohol, sorbitane fatty acid esters, polyoxyethylene sorbitane fatty acid esters, polyoxyethylene fatty acid esters, monoglycerides and diglycerides, lecithin or mixtures thereof.

Perfumes and/or flavour-improving substances which may be mentioned are: ethereal vegetable oils, for example from fennel or aniseed.

Additives and, in particular, thickeners are used for the preparation of the endoparasiticidal pastes according to the invention if liquid carriers (for example liquid paraffins) are employed as the carriers. In this case, these thickeners are then necessary to achieve the paste-like consistency.

By paste there is to be understood a soft, semi-solid formulation which contains, in a liquid medium, an insoluble solid as the disperse phase. The paste should stick in the mouth of the horse as much as possible. The Gasterophilus larvae living in the mouth of horses are attacked particularly readily by the paste form, since some of the paste distributes itself in the mouth of the animal and the larvae are killed there.

The water content of the endoparasiticidal pastes according to the invention can be determined by methods which are in themselves known (for example the Karl-Fischer titration).

The active compounds employed in the preparation of the endoparasiticidal pastes according to the invention are preferably used in the following particle sizes: Trichlorfon: minimum size of the crystals: about 10 $\mu$m; crystals with a size of 30 to 200 $\mu$m are preferably employed. Febantel: maximum particle size: up to about 30 $\mu$m; particle sizes of 0.5 to 10 $\mu$m are preferably employed.

The present invention further provides a process for the production of endoparasiticidal pastes of the invention in which Trichlorofon and Febantel are formulated to a paste using liquid and/or semi-solid carrier(s) with or without one or more additives, specifically by mixing the constituents with one another in any desired sequence or also in a particular sequence, depending on the nature of the liquid and/or semi-solid carriers and on the additives optionally used.

The preparation procedures illustrated in Examples 1 to 3 are particularly preferred.

The present invention further relates to a process for combating endoparasites, especially roundworm and immature stages thereof or Gastrophilus larvae, in horses which comprises administering to the horse a endoparasitical paste of the present invention.

The endoparasiticidal pastes according to the invention are advantageously in each case dosed so that 10 to 50, preferably 15 to 40, mg of Trichlorfon and 0.1 to 10, preferably 1 to 6, mg of Febantel are administered through the paste (preferably by injection, with the aid of a paste injector, into the mouth of the horse) per kg of body weight of the horse. As a rule, a single dosage is sufficient to achieve the desired effect (that is to say destruction of the endoparasites living, above all, in the mouth and in the gastro-intestinal tract and in the lungs of the horse).

The following Examples 1 to 3 illustrate pastes according to the present invention and processes for their production and Example 4 illustrates the use of pastes of the present invention.

EXAMPLE 1

Constituents of a paste preparation according to the present invention are as follows:

| | | |
|---|---|---|
| A | Febantel active compound (average particle size: 2-5 μm) | 8.6 kg |
| B | Trichlorfon active compound (average particle size: 50-100 μm) | 47.9 kg |
| C | Emulsifying wax based on cetyl-stearyl alcohol mixed with sodium lauryl-sulphate (Emulsifying Wax BP 73) | 2.5 kg |
| D | Colloidal silicic acid | 2.6 kg |
| E | Petroleum jelly (white) | 1.5 kg |
| F | Thin liquid paraffin (according to DAB VII)* | 46.4 kg |
| | Total amount | 109.5 kg |

*DAB VII: Deutsches Arzneibuch (German Pharmacopia), 7th edition, Stuttgart 1968

These 109.5 kg correspond to 100 liters of paste preparation.

The paste formulation with the constituents indicated above is prepared as follows:

(1) The emulsifying wax (C), the white petroleum jelly (E) and the thin liquid paraffin (F) are introduced into a kettle which can be heated and is provided with a stirrer.

(2) The mixture of C, E and F is warmed to approximately 80° C. and stirred until a homogeneous solution has formed.

(3) The mixture is then cooled to a temperature of about 60° C., whilst stirring.

(4) The active compound Trichlorfon (B) is added to the solution obtained according to (3) and distributed homogeneously therein with a rotor-stator disperser (for example Ultra-Turrax).

(5) The active compound Febantel (A) and the colloidal silicic acid (D) are added to (4) and homogeneously distributed therein.

(6) The paste is obtained via a homogeniser.

(7) The paste is then preferably filled into injectors for administration.

EXAMPLE 2

Constituents:

| | | |
|---|---|---|
| A | Febantel active compound (average particle size: 2-5 μm) | 8.6 kg |
| B | Trichlorfon active compound (average particle size: 50-100 μm) | 41.1 kg |
| C | Emulsifying wax based on cetyl-stearyl alcohol mixed with sodium lauryl-sulphate (Emulsifying Wax BP 73) | 2.5 kg |
| D | Colloidal silicic acid | 2.6 kg |
| E | Petroleum jelly (white) | 1.5 kg |
| F | Thin liquid paraffin (according to DAB VII) | 52.7 kg |
| | Total amount | 109.0 kg |

The paste is prepared and filled into injectors analogously to that in Example 1.

EXAMPLE 3

Constituents:

| | | |
|---|---|---|
| A | Febantel active compound (average particle size: 2-5 μm) | 4.3 kg |
| B | Trichlorfon active compound (average particle size: 50-100 μm) | 20.5 kg |
| C | Thick liquid paraffin | 50.0 kg |
| D | Petroleum jelly (white) according to DAB VII | 10.0 kg |
| | Total amount | 84.8 kg |

The petroleum jelly (D) is dissolved in the thick liquid paraffin (C), whilst warming to 30° to 40° C. The constituents A (Febantel active compound) and B (Trichlorfon active compound) are slowly stirred into the solution formed, the mixture is then homogenized in a homogeniser and the paste is filled into injectors for administration.

EXAMPLE 4

In a comparative experiment, three paste formulations are tested comparatively on horses severly infested by Strongylidae (species of roundworm) using a dosing instrument (so-called "dosing injector"). The paste formulations are in each case paste formulations which contain, as the active compound, (a) only Trichlorfon, (b) only Febantel or (c) a Trichlorfon/Febantel mixture according to the invention.

In the cases (a), (b) and (c), the paste base is the same and consists of components (C), (D), (E) and (F) according to Example 2. The ratio of active compounds in the paste formulation (c) is 1 part by weight of Febantel to 30 parts by weight of Trichlorfon.

In the horse test, pastes (a), (b) and (c) are administered, with the aid of the dosing injector in an amount such that just 30 mg of the active compound Trichlorfon are employed per kg of body weight of the horse and just 1 mg of the active compound Febantel is employed per kg of body weight of the horse.

Proof of the activity is established with the aid of the Strongylidae egg reduction test. The activity against large and small Strongylidae of horses is recorded, and a noticeable synergistic (that is to say superadditive) effect on the reduction of the parasites is achieved when the Trichlorfon/Febantel paste (c) according to the invention is used, in comparison to the monopastes (a) and (b).

What is claimed is:

1. An endoparasiticidal paste for horses, which comprises a mixture of 2,2,2-trichloro-1-hydroxyethylphosphonic acid dimethyl ester and N-(2-methoxyacetamido-4-phenylthio-phenyl)-N',N"-bis-methoxy-carbonylguanidine and a water content of less than one percent by weight, relative to the total composition of the endoparasiticidal paste.

2. An endoparasiticidal paste according to claim 1, which comprises 5 to 70 parts by weight of 2,2,2-trichloro-1-hydroxyethyl-phosphonic acid dimethyl ester, 0.5 to 10 parts by weight of N-(2-methoxyacetamido-4-phenylthiophenyl)-N',N"-bis-methoxy-carbonlguanidine, 20 to 70 parts by weight of liquid and/or semisolid carrier(s), 0 to 20 parts by weight of one or more additives and less than 1 part by weight of water.

3. An endoparasiticidal paste according to claim 2, which contains 20 to 60 parts by weight of 2,2,2-trichloro-1-hydroxyethyl-phosphonic acid dimethyl ester, 2 to 8 parts by weight of N-(2-methoxyacetamido-4-phenylthio phenyl)-N',N" bis methoxy-carbonlguanidine, 30 to 60 parts by weight of liquid and/or semisolid carrier(s), 0 to 10 parts by weight of one or more additives and less than 0.5 part by weight of water.

4. A process for the production of an endoparasiticidal paste for horses as claimed in claim 1, which comprises formulating into a paste 2,2,2-trichloro-1-hydroxyethyl-phosphonic acid dimethyl ester and N-(2-methoxyacetamido-4-phenylthio phenyl)-N',N''-bis-methoxycarbonlguanidine using liquid and/or semi-solid carrier(s) with or without one or more additives.

5. A process according to claim 4, in which 5 to 70 parts by weight of 2,2,2-trichloro-1-hydroxyethyl-phosphonic acid dimethyl ester, 0.5 to 10 parts by weight of N-(2-methoxyacetamido-4-phenylthio-phenyl)-N',N''-bis-methoxy-carbonlguanidine, 20 to 70 parts by weight of liquid and/or semi-solid carriers and 0 to 20 parts by weight of additives are used.

6. A method of combating endoparasites in horses which comprises administering to the horse an endoparasiticidally effective amount of a paste according to claim 1.

7. A method of combating roundworm and immature stages thereof or Gastrophilus larvae in horses which comprises administering to the horse an endoparasiticidally effective amount of a paste according to claim 1.

8. A method according to claim 6 or 7 in which each dose administered contains 15 to 40 mg of 2,2,2-trichloro-1-hydroxyethyl-phosphonic acid dimethyl ester and 1 to 6 mg of N-(2-methoxyacetamido-4-phenylthio-phenyl)-N',N''-bis-methoxy-carbonlguanidine per kg of body weight of the horse.

* * * * *